United States Patent [19]

Schutte et al.

[11] Patent Number: 5,026,385
[45] Date of Patent: Jun. 25, 1991

[54] DOUBLE-BLADED SCALPEL

[76] Inventors: Michael J. Schutte; Jerry J. King, both of 2825 Fort Missoula Rd., Missoula, Mont. 59801

[21] Appl. No.: 503,706
[22] Filed: Apr. 3, 1990
[51] Int. Cl.⁵ .............................................. A61B 17/32
[52] U.S. Cl. ....................................... 606/167; 30/304
[58] Field of Search ............... 606/167, 170, 183, 160, 606/166; 30/173, 304, 113.1, 121

[56] References Cited

U.S. PATENT DOCUMENTS

| | | | |
|---|---|---|---|
| 479,102 | 7/1892 | Willbrandt | 30/343 |
| 3,452,754 | 7/1969 | Stayer | 128/305 |
| 3,998,229 | 12/1976 | Barton | 606/167 |
| 4,578,865 | 4/1986 | Keuer | 30/304 |
| 4,688,570 | 8/1987 | Kramer et al. | 606/166 |

FOREIGN PATENT DOCUMENTS 2637172 2/1978 Fed. Rep. of Germany ........ 30/343

Primary Examiner—C. Fred Rosenbaum
Assistant Examiner—William W. Lewis
Attorney, Agent, or Firm—Wells, St. John & Roberts

[57] ABSTRACT

A double-bladed scalpel for removal of tissues requiring consistent width along their length. Identical metal scalpel blades are embedded within an integral rigid supporting handle. The two blades protrude outwardly from one bifurcated handle end. A contoured finger rest permits the user to exert substantial cutting pressure when using the scalpel in applications where scribing of bony tissue is required.

9 Claims, 2 Drawing Sheets

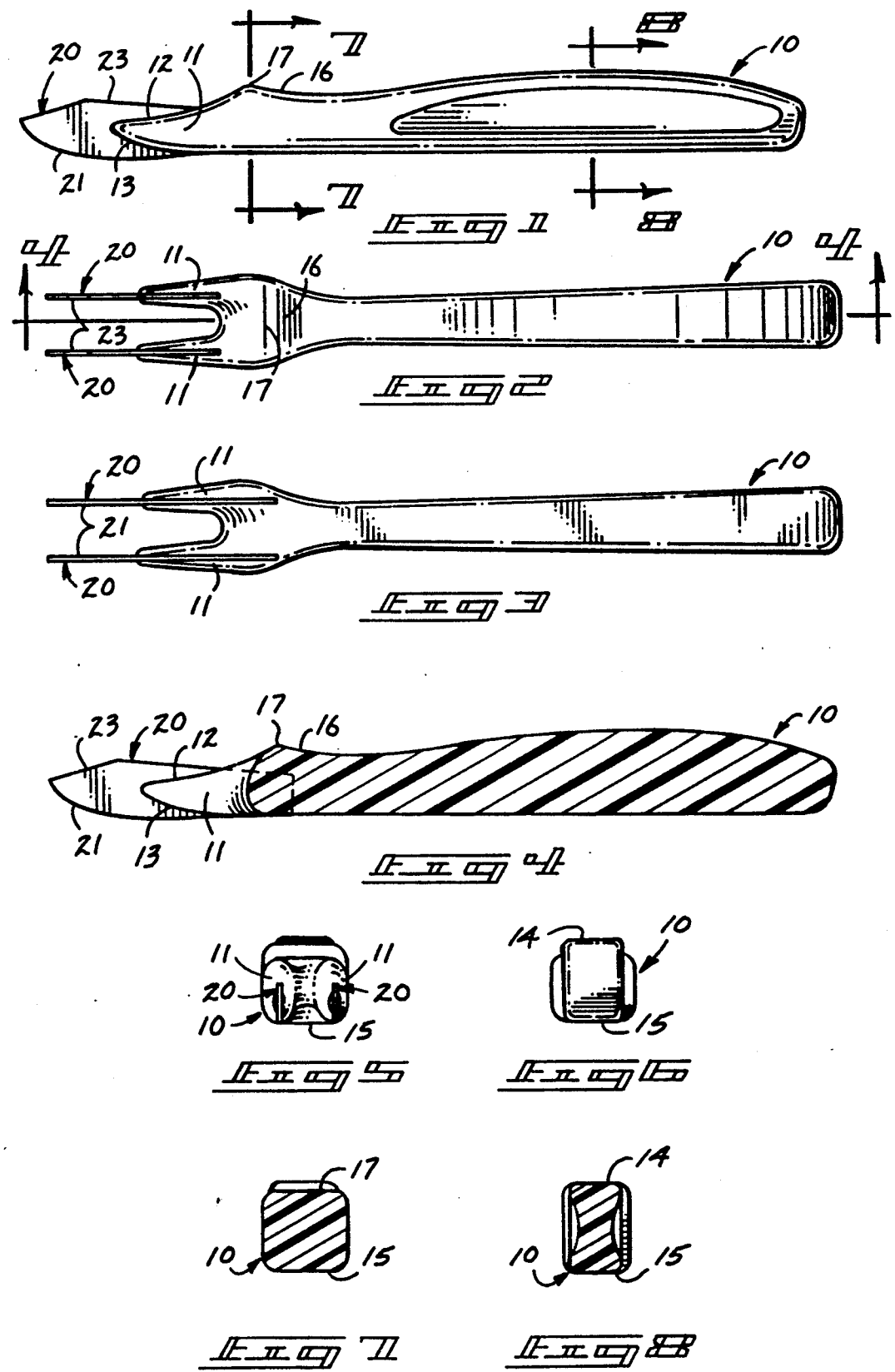

DOUBLE-BLADED SCALPEL

TECHNICAL FIELD

This invention pertains to surgical scalpels having two blades for producing parallel incisions through tissue.

BACKGROUND OF THE INVENTION

The present double-bladed scalpel was designed specifically for use in reconstruction of the anterior cruciate ligament in the knee. In this procedure, a strip of patellar tendon measuring between 10 to 12 millimeters in width is harvested from the middle of the tendon. The strip of tissue must be consistent in width to provide maximum strength in the resulting graft.

Current techniques for harvesting such strips of tissue require making two separate incisions in succession, the second incision being guided by manually holding a ruler parallel to the first. This typically results in a graft that varies in width along its length. The differences in width from one point to another along the graft can range up to three millimeters.

When making sequential incisions along a tendon such as this, the tension within the tendon is modified after production of the first incision. The changes in tension affect the consistency of the second incision in a pattern that cannot be predetermined. It was recognized that if one could simultaneously produce the two incisions along opposite sides of the tendon, the tension encountered within the tendon would then be constant and not affect the width of the resulting strip.

The initial efforts to produce two parallel incisions that lead to this development were accomplished by attempting to attach two conventional scalpels to one another in spaced parallel positions. While this constituted an improvement over the prodution of separate incisions, undesirable deviations in graft width continued to be encountered. Such variations in width are particularly difficult to prevent in the above-described surgical procedure, where the strip of patellar tendon is harvested along the middle of its underlying bone. The bony surfaces are curved and tend to splay two surgical blades outwardly from one another in response to the cutting pressures necessary to scribe the bone.

The present invention was developed in an effort to rigidly support two surgical blades for such procedures. It assures that sufficient pressure can be simultaneously applied to them to scribe underlying bone when this is required.

THE DRAWINGS

The preferred embodiment of the invention is illustrated in the accompanying drawings, in which:

FIG. 1 is a side view of a scalpel;
FIG. 2 is a top view;
FIG. 3 is a bottom view;
FIG. 4 is a longitudinal sectional view taken along line 4—4 in FIG. 2;
FIG. 5 is a left hand end view;
FIG. 6 is a right and end view;
FIG. 7 is a cross-sectional view taken along line 7—7 in FIG. 1;
FIG. 8 is a sectional view taken along line 8—8 in FIG. 1;
FIG. 9 is a diagrammatic side view showing the manner by which the scalpel is gripped by a user; and
FIG. 10 is a similar diagrammatic top view.

DETAILED DESCRIPTION OF THE PREFERRED EMBODIMENTS

Figure 9:
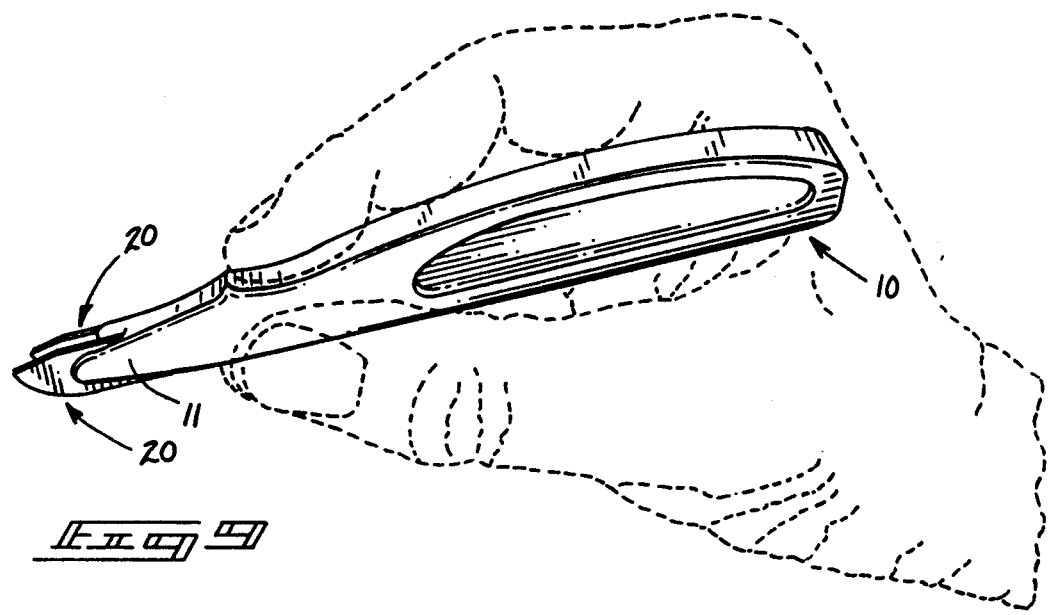

The following disclosure of the invention is submitted in furtherance with the consititutional purpose of the Patent Laws "to promote the progress of science and useful arts" (Article 1, Section 8).

FIGS. 1—8 illustrate features of a single-use, double-bladed scalpel according to this disclosure. It was designed specifically for harvesting a strip of patellar tendon during reconstruction of the anterior cruciate ligament in the knee. This surgical procedure is well known and further details concerning the application of such graft is not believed to be necessary to an understanding of the present invention.

The scalpel comprises an elongated handle 10 formed integrally of solid rigid material. It is preferably molded from rigid plastic resins.

The scalpel is provided with a pair of identical elongated surgical cutting blades 20. Each blade has a sharpened lower edge 21 that extends to an outer blade end. The lower edge 21 of each blade is substantially flush with the bottom surface 13 of handle 10 to present a scalpel having a sharpened lower edge 21 that smoothly merges into the bottom surface 13 along the handle 10.

Each blade 20 also includes an upper edge extending along its length from the inner end attached to handle 10 to its outer end, where it joins the sharpened lower edge 21. The upper edge 23 of each blade 20 is embedded within the handle structure and is spaced from the upper surface 12 of handle 10 (see FIG. 1).

The blades each also include an inner blade end 22. The inner blade ends 22 are individually fixed to the handle 10 in parallel side by side positions protruding outwardly from one handle end. The blades are preferable mounted in the handle in a permanent manner, but can be replaceably mounted if desired.

The one end of the elongated handle 10 that mounts the two blades 20 is bifurcated to present two rigid spaced extensions 11. Each extension 11 has upper and lower surfaces 14 and 15, respectively. They individually amount the two blades 20 with the upper surface 14 of each extension covering the upper edge 23 of the blade 20 mounted within it. The lower surface 15 of each extension recedes upwardly and outwardly from the lower edge 21 of the blade 20 (see FIG. 1).

The inner end 22 of each blade 20 is substantially overlapped at each of its sides by its supporting extension 11. As can be seen in the drawings, approximately one-half of the longitudinal length of each blade 20 is overlapped by the elongated handle 10. The resulting longitudinal overlap between the rigid extensions 11 of handle 10 and each blade 20 mounted within it serves to prevent outward splaying of the protruding blade portions.

When applying the present invention to a single-use scalpel, each blade 20 is permanently embedded within the elongated handle 10. This can be accomplished either by molding the handle structure about the metal blades or by molding blade slots within the handle extensions 11 and assembling the scalpel by subsequently inserting the blades 20 after molding of the handle 10. Such fabrication requires the production of a permanent connection between the handle 10 and each blade 20. This can be accomplished by use of a suitable adhesive compatible with the involved respective materials.

In order to facilitate scribing of underlying bone as a strip of tendon is being cut, it is desirable that substantial finger pressure be directed to the two blades 20. This is accomplished by shaping the handle 10 to present an exterior surface that fits the hand of a user when grasped in a pencil-like grip during harvesting of a strip of tissue requiring parallel edges. The manner by which the handle 10 is grasped is illustrated in FIGS. 8 and 9.

The handle 10 presents the user with a relatively thick and substantial structure in comparison to the usual thin handle of a conventional scalpel. It is contoured to provide a comfortable fit in the hand of a user. Its cross-sectional shape is in the form of a thickened rectangle. The thickened rectangular shape of the handle assists in preventing twisting within the hands of a user.

Figure 10:
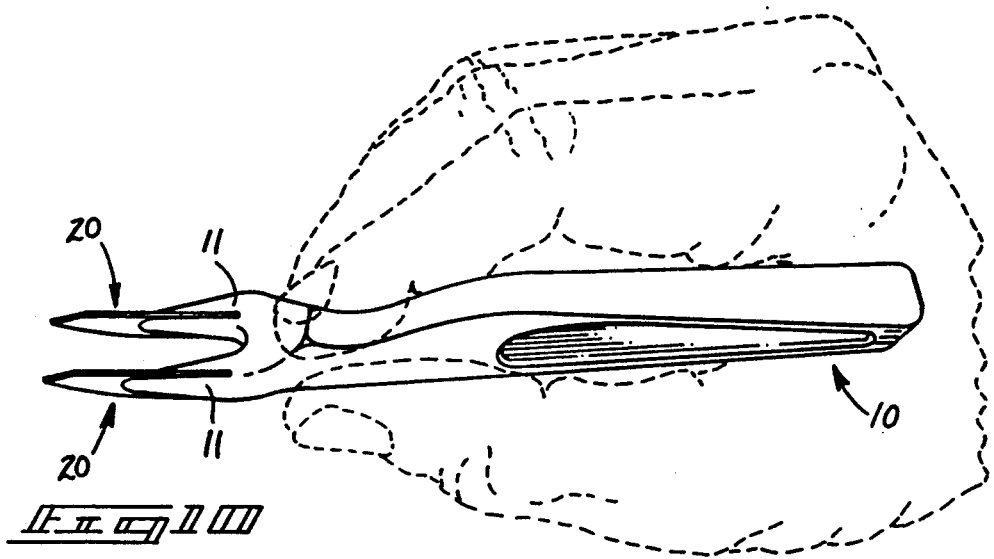

Handle 10 includes a contoured finger rest 16 extending across its upper surface 12 at a location inwardly adjacent to the one end of handle 10 that mounts the two blades 20. The finger rest 16 is defined by a transverse ridge 17 extending across the full width of the handle 10. The ridge 17 provides an abutment for the index finger of a user (See FIGS. 9 and 10). This allows substantial downward pressure to be exerted by the end of the finger to urge the blades 20 into the tissue being cut. To assure that this finger pressure is applied directly to the blades 20, it is preferable that the inner ends of blades 20 be located within the handle 10 at a longitudinal position under the finger rest 16. (See FIGS. 1 and 2).

The above structure provides an extremely rigid construction for supporting the parallel cutting blades 20. The support for blades 20 is adequate to prevent them from splaying while scribing the underlying bone beneath a tendon, where considerable force is often exerted between the hand of the user and the bone.

The present invention also readily lends itself to production from disposable plastic resins, such as polycarbonate. Designing a disposable scalpel for single-use purposes helps to prevent any potential In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A double bladed scalpel, comprising:
a rigid elongated solid handle formed integrally of plastic resin material;
a pair of identical elongated metal cutting blades outwardly protruding from one end of the handle in transversely-spaced parallel side-by-side positions across the handle, each blade having a sharpenend lower edge extending to an outer blade end;
the blades each having an inner blade end, the inner blade ends of the two blades being permanently connected to the one end of the handle;
the one end of the elongated handle being bifurcated into two integral rigid extensions having lengths less than the lengths of the blades and being arranged in transversely-spaced parallel side-by-side positions across the one end of the handle, each extension substantially overlapping and individually supporting one of the blades to prevent splaying of the outwardly protruding blade portions.

2. The double-bladed scalpel of claim 1 further comprising:
a finger rest adjacent to the bifurcated parallel side-by-side extensions to enable the user to apply substantial downward pressure on the extensions and blades.

3. A double-bladed scalpel comprising:
a rigid elongated handle formed integrally of solid plastic resin material;
a pair of identical elongated metal cutting blades, each blade having a sharpened lower edge extending to an outer blade end;
the blades each having an inner blade end, the inner blade ends of the two blades being permanently connected to one end of the handle in parallel side-by-side positions protruding outwardly from one handle end;
the one end of the elongated handle being bifurcated into two integral rigid extensions, each extension individually supporting one of the blades;
the elongated handle including a contoured finger rest formed across its upper surface, the finger rest terminating in a transverse ridge extending across the full width of the handle at a location inwardly adjacent to its one end;
the inner ends of the blades being located within the handle at a longitudinal position under the finger rest.

4. A double bladed scalpel, comprising:
a rigid elongated solid handle formed integrally of plastic resin material, the handle having an exterior cross-sectional shape in the form of a thickened rectangle to fit a user's hand when grasped in a
pencil-like grip and to assist in preventing twisting of the handle within the hands of a user during harvesting of a strip of tissue requiring parallel edges;
a pair of identical elongated metal cutting blades outwardly protruding from one end of the handle in transversely-spaced parallel side-by-side positions across the handle, each blade having an elongated upper edge and an elongated lower edge, the lower edge of each blade being sharpened and extending to an outer blade end at which it meets the upper edge;
the blades each having an inner blade end, the inner blade ends being permanently connected to the one end of the handle;
the one end of the elongated handle being bifurcated into two integral rigid extensions having lengths less than the lengths of the blades and being arranged in transversely-spaced parallel side-by-side positions across the handle, each extension substantially overlapping and individually supporting one of the blades to prevent splaying of the outwardly protruding blade portions.

5. The double-bladed scalpel of claim 4 further comprising:
a finger rest adjacent to the bifurcated parallel side-by-side extensions to enable the user to apply substantial downward pressure on the extensions and blades.

6. A double-bladed scalpel, comprising:
a rigid elongated handle formed integrally of solid plastic resin material, the handle having an exterior cross-sectional shape in the form of a thickened rectangle to fit a user's hand when grasped in a pencil-like grip and to assist in preventing twisting of the handle within the hands of a user during harvesting of a strip of tissue requiring parallel edges;

a pair of identical metal cutting blades, each blade having an elongated upper edge and an elongated lower edge, the lower edge of each blade being sharpened and extending to an outer blade end at which it meets the upper edge;

the blades each having an inner blade end, the inner blade ends being permanently connected to one end of the handle in parallel side-by-side positions protruding longitudinally outward from the handle;

the one end of the elongated handle being bifurcated into two integral rigid extensions, each extension individually supporting one of the blades;

the elongated handle including a contoured finger rest formed across its upper surface, the finger rest terminating in a transverse ridge extending across the full width of the handle at a location inwardly adjacent to its one end;

the inner ends of the blades being located within the handle at a longitudinal position under the finger rest.

7. A single-use double bladed scalpel, comprising:

a contoured rigid solid elongated handle formed integrally of plastic resin material, the handle having an exterior cross-sectional shape in the form of a thickened rectangle shaped to fit a user's hand when grasped in a pencil-like grip and to assist in preventing twisting of the handle within the hands of a user during harvesting of a strip of patellar tendon tissue and an adjacent strip of bone from the tibial tuberosity where consistency in width is required on the harvested tissue to assure maximum strength in the resulting graft;

a pair of identical metal cutting blades outwardly protruding from one end of the handle in transversely-spaced parallel side-by-side positions across the handle, each blade having an elongated upper edge and an elongated lower edge, the lower edge of each blade being sharpened and extending to an outer blade end at which it meets the upper edge;

the blades each having an inner blade end, the inner blade ends being permanently connected to the one end of the handle with portions of their respective lower edges protruding longitudinally outwardly from the one handle end, the inner end of each blade being substantially overlapped at each of its sides by the one handle end to prevent splaying of the protruding blade portions while scribing bony tissue underlying the harvested tendon;

the one end of the elongated handle being bifurcated into two integral rigid extensions having lengths less than the lengths of the blades and being arranged in transversely-spaced parallel side-by-side positions across the one end of the handle, each extension substantially overlapping and individually supporting one of the blades to prevent splaying of the outwardly protruding blade portions during harvesting of graft tissue in anterior cruciate ligament reconstructive surgery.

8. The double-bladed scalpel of claim 7 further comprising:

a finger rest adjacent to the bifurcated parallel side-by-side extensions to enable the user to apply substantial downward pressure on the extensions and blades.

9. A single-use double-bladed scalpel for the harvesting of graft tissue in anterior cruciate ligament reconstructive surgery, comprising:

a contoured rigid elongated handle formed integrally of solid plastic resin material, the handle having an exterior cross-sectional shape in the form of a thickened rectangle shaped to fit a user's hand when grasped in a pencil-like grip and assist in preventing twisting of the handle within the hands of the user during harvesting of a strip of patellar tendon tissue and an adjacent strip of bone from the tibial tuberosity requiring consistency in width for maximum strength in the resulting graft;

a pair of identical metal cutting blades, each blade having an elongated upper edge and an elongated lower edge, the lower edge of each blade being sharpened and extending to an outer blade end at which it meets the upper edge;

the blades each having an inner blade end, the inner blade ends being permanently connected to one end of the handle in parallel side-by-side positions with portions of their respective lower edge protruding longitudinally outward from the one handle end, the inner end of each blade being substantially overlapped at each of its side by the one handle end to prevent splaying of the protruding blade portions while scribing bony tissue underlying the harvested tendon;

the one end of the elongated handle being bifurcated into two integral rigid extensions, each extension individually supporting one of the blades;

the elongated handle including a contoured finger rest formed across its upper surface, the finger rest terminating in a transverse ridge extending across the full width of the handle at a location inwardly adjacent to its one end;

the inner ends of the blades being located within the handle in a longitudinal position under the finger rest.

* * * * *